(12) United States Patent
Peivareh et al.

(10) Patent No.: US 11,321,917 B1
(45) Date of Patent: May 3, 2022

(54) SYSTEMS, METHODS AND APPARATUS FOR CALCULATING POSITION AND ROTATION FROM A MANUALLY SET REFERENCE POINT IN A SPATIAL MESH

(71) Applicant: apoQlar GmbH, Hamburg (DE)

(72) Inventors: Kevin Peivareh, Hamburg (DE); Sirko Pelzl, Hamburg (DE); Simon Furrer, Hamburg (DE)

(73) Assignee: apoQlar GmbH, Hamburg (DE)

( * ) Notice: Subject to any disclaimer, the term of this patent is extended or adjusted under 35 U.S.C. 154(b) by 0 days.

(21) Appl. No.: 17/339,939

(22) Filed: Jun. 4, 2021

(51) Int. Cl.
 G06T 17/20 (2006.01)
 G06T 7/73 (2017.01)
 G06T 19/00 (2011.01)

(52) U.S. Cl.
 CPC .......... *G06T 17/20* (2013.01); *G06T 7/74* (2017.01); *G06T 19/006* (2013.01); *G06T 2210/41* (2013.01)

(58) Field of Classification Search
 None
 See application file for complete search history.

(56) References Cited

U.S. PATENT DOCUMENTS

2017/0312032 A1\* 11/2017 Amanatullah ......... G09B 23/30

\* cited by examiner

Primary Examiner — Nicholas R Wilson
(74) Attorney, Agent, or Firm — Michael G. Smith, Esq.

(57) ABSTRACT

Systems, methods and apparatus are provided through which a 3D source mesh object is generated by a three-dimensional-augmented-reality engine from medical data, a copy mesh object is generated by copying the 3D source mesh object, a center of the 3D source mesh object is calculated from the 3D source mesh object, an orientation bar is generated and placed orthogonally in the center of the copy mesh object, a scene mesh object a generated by scanning the room, the scene mesh object being a game object, a patient mesh object is generated by cutting the scene mesh object in reference to original dimensions of the 3D source mesh object and a patient mesh object is generated from the patient mesh object by starting from the index tip of a finger and placing the 3D source mesh object in a direction that is downwards.

12 Claims, 21 Drawing Sheets

SOURCE MESH OBJECT 300

YELLOW ORIENTATION BAR 400

SCENE MESH 500

PATIENT MESH 600

REFERENCE POINT PICKER OBJECT 1400

US 11,321,917 B1

SYSTEMS, METHODS AND APPARATUS FOR CALCULATING POSITION AND ROTATION FROM A MANUALLY SET REFERENCE POINT IN A SPATIAL MESH

FIELD

This disclosure relates generally to healthcare augmented reality.

BACKGROUND

Conventional augmented reality healthcare systems use artificial intelligence algorithms to detect the patient or other objects and to calculate the corresponding position and rotation for the placement in three dimensions. The artificial intelligence algorithms tend to be slow in execution and expensive and complicated to develop.

BRIEF DESCRIPTION

The above-mentioned shortcomings, disadvantages and problems are addressed herein, which will be understood by reading and studying the following specification.

In some implementations, a display of a mixed reality scene of a human includes a mesh object of a portion of the human is rotated in reference to two points, the rightmost and the leftmost points of the portion of the patient mesh object, in which the rotated mesh object is defined in terms of x, y and z coordinates. This process is much faster with less engineering complexity than the artificial intelligence algorithms of the conventional augmented reality healthcare systems.

Apparatus, systems, and methods of varying scope are described herein. In addition to the aspects and advantages described in this summary, further aspects and advantages will become apparent by reference to the drawings and by reading the detailed description that follows.

DETAILED DESCRIPTION

In the following detailed description, reference is made to the accompanying drawings that form a part hereof, and in which is shown by way of illustration specific implementations which may be practiced. These implementations are described in sufficient detail to enable those skilled in the art to practice the implementations, and it is to be understood that other implementations may be utilized and that logical, mechanical, electrical and other changes may be made without departing from the scope of the implementations. The following detailed description is, therefore, not to be taken in a limiting sense.

The detailed description is divided into four sections. In the first section, apparatus of implementations are described. In the second section, implementations of methods are described. In the third section, hardware and the operating environments in conjunction with which implementations may be practiced are described. Finally, in the fourth section, a conclusion of the detailed description is provided.

Apparatus Implementations

In the previous section, a system level overview of the operation of an implementation was described. In this section, the particular apparatus of such an implementation are described by reference to a series of diagrams.

Figure 1:
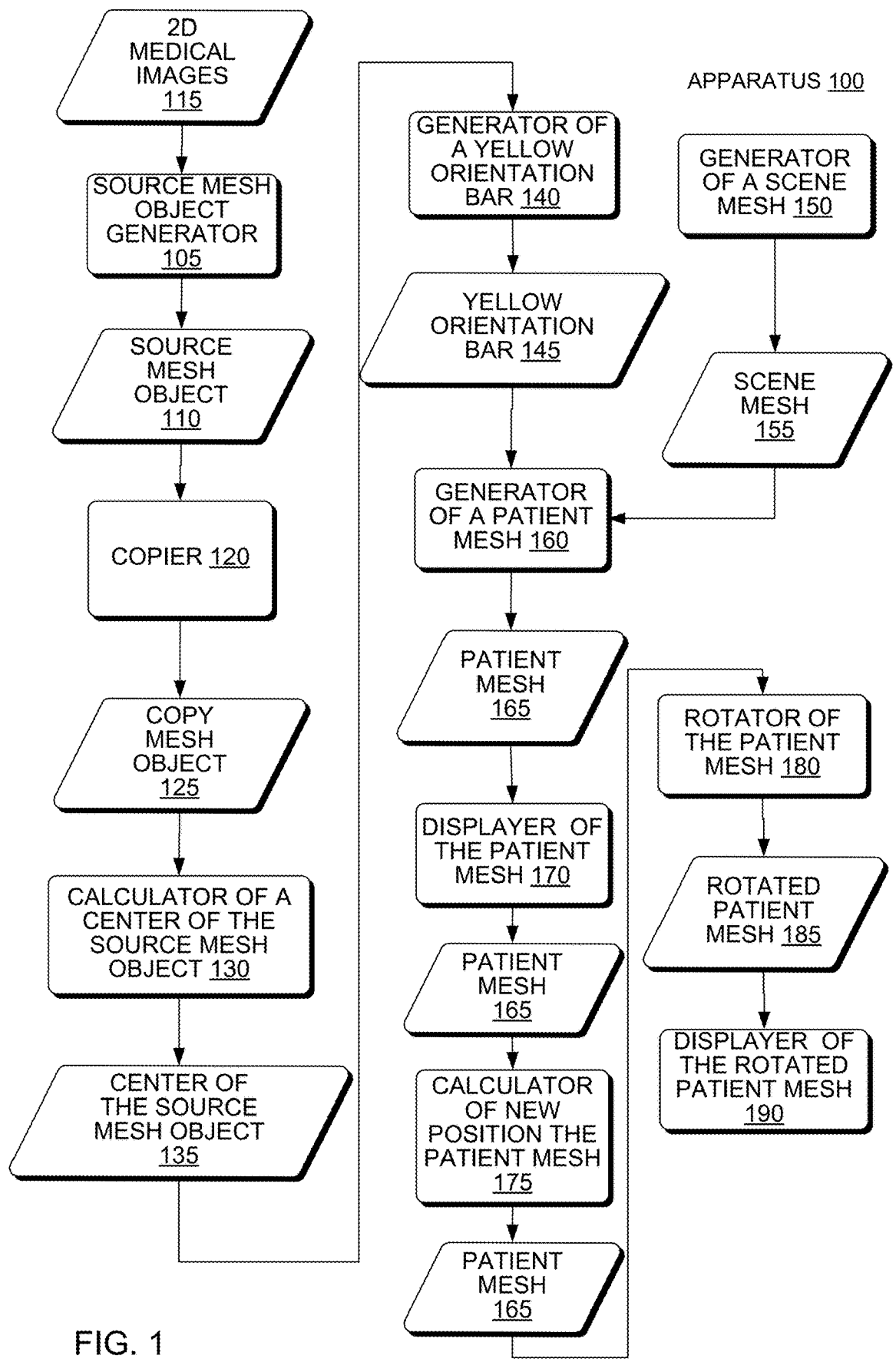
FIG. 1 is a block diagram of an apparatus of augmented reality, according to an implementation.

FIG. 1 is a block diagram of an apparatus 100 of augmented reality, according to an implementation.

The apparatus 100 includes a generator 105 of a 3D source mesh object 110 from two-dimensional (2D) or three-dimensional (3D) medical image data 115.

The 2D medical images can be computed tomography (CT) scan data, optical coherence tomography (OCT), positron emission tomography (PET) computed tomography (CT), a combination of a single photon emission computed tomography scan with a computed tomography (SPEC CT), XR, cone-beam computed tomography (CBCT), magnetic resonance image (MRI) scan data, optical coherence tomography (OCT), positron emission tomography-computed tomography (PETCT) or medical imaging scan data. The 2D medical images are stored in DICOM® format, and some 3D data is stored in OBJ, STL or PLY formats, which encode the 3D model's geometry. STL format uses "approximate mesh object" encoding, which uses tessellation which is the process of tiling a surface of an object with geometric shapes. The tiling produces no overlaps or gaps. The tiles used are triangles (called facets), which cover the surface of the 2D shape. OBJ and PLY formats both use "precise mesh object" encoding which use tessellation with polygonal facets, freeform curves and freeform surface patches, that stores the appearance of the model and other details such as color or texture.

The 3D source mesh object 110 is a collection of points connected with lines drawn between them that represent a system's view of a 3D object. In general, the 3D source mesh object 110 can be composed of 4 types of elements: tetrahedrons (4 corners), wedges (6 corners), hexahedrons (8 corners) and pyramids (5 corners). In some implementations, the 3D source mesh object 110 is generated by a three-dimensional-augmented-reality engine (such as the Unity 3D AR engine) from the medical images, in which case the 3D source mesh object 110 is a Game Object in Unity. A Game Object is a fundamental object that represent characters, props and scenery, and which acts as a container for components which define behavior and implement functionality. In some implementations, the 3D source mesh object 110 is encoded in a byte format. One example of 3D source mesh object 110 is 3D source mesh object 300 in FIG. 3.

The apparatus 100 also includes a copier 120 of the 3D source mesh object 110, yielding a copy mesh object 125.

The apparatus 100 includes a calculator 130 of a center 135 of the 3D source mesh object 110.

Figure 4:
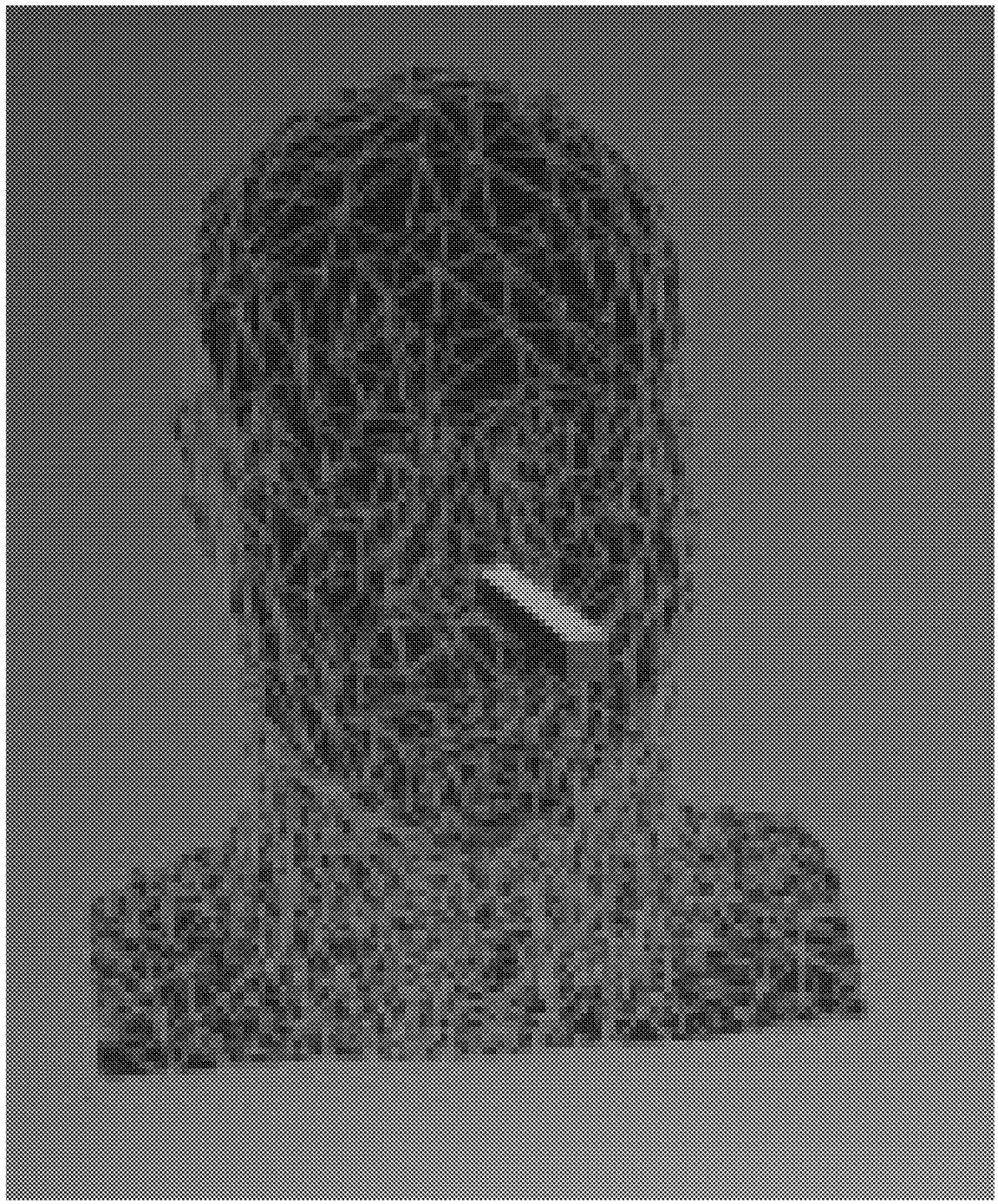
FIG. 4 is a visual depiction of a yellow orientation bar, according to an implementation.

Apparatus 100 also includes a generator 140 of an orientation bar 145 that is placed orthogonally in the center of the copy mesh object 125. In some implementations, such as shown in FIG. 4, the orientation bar is yellow colored and between 10 cm and 1 meter in length. In other implementations, the color of the orientation bar is a color other than yellow.

Apparatus 100 also includes a generator 150 of a scene mesh object 155. In some implementations, the examination room is scanned by a mixed reality smartglass, such as the Microsoft HoloLens® device, to obtain the scene mesh object 155. In some implementations, the scene mesh object 155 is a Game Object in Unity, which the Scene Understanding software development toolkit transforms unstructured environment data from the room scan and converts the unstructured environment data in the room scan into an abstract representation. One example of the scene mesh object is scene mesh object 500 in FIG. 5.

Thereafter, in some implementations the operator initiates the placement calculations, such as by pressing a relevant button with their left index finger, while manually placing their right index fingertip on the center location that was marked in step 1725 on the patient body. Alternatively, can use pinch and hold just with the right index and thumb finger to initiate the operator.

Apparatus 100 includes a generator 160 of a patient mesh object 165 that cuts the scene mesh object 155 in reference to original dimensions of the 3D source mesh object (by placing the 3D source mesh object downwards by half the depth of the 3D source mesh object respective to each axis and the orientation of the patient), the initial orientation of the human from the operator, the original size from the 3D source mesh object, and the location marked by the operator's right index fingertip. One example of the patient mesh object 165 is patient mesh object 600 in FIG. 6.

Apparatus 100 includes a displayer 170 of the patient mesh object 165. The displayed patient mesh object 165 includes the yellow orientation bar 145. The orientation bar 145 can be another other color.

Apparatus 100 includes a calculator 175 of a new position of the patient mesh object 165 in terms of x, y and z coordinates.

Apparatus 100 includes a rotator 180 of the patient mesh object 165, yielding a rotated patient mesh object 185. The patient mesh object 165 is rotated in reference to two points, the rightmost and the leftmost points from the patient mesh object 165.

Apparatus 100 includes a displayer 190 of the rotated patient mesh object 185. The displayed patient mesh object includes the yellow orientation bar 145.

Apparatus 100 can be implemented as a component of a mixed reality smartglass such as the Microsoft Hololens®, or another device such as the Microsoft Kinect® device.

Figure 2:
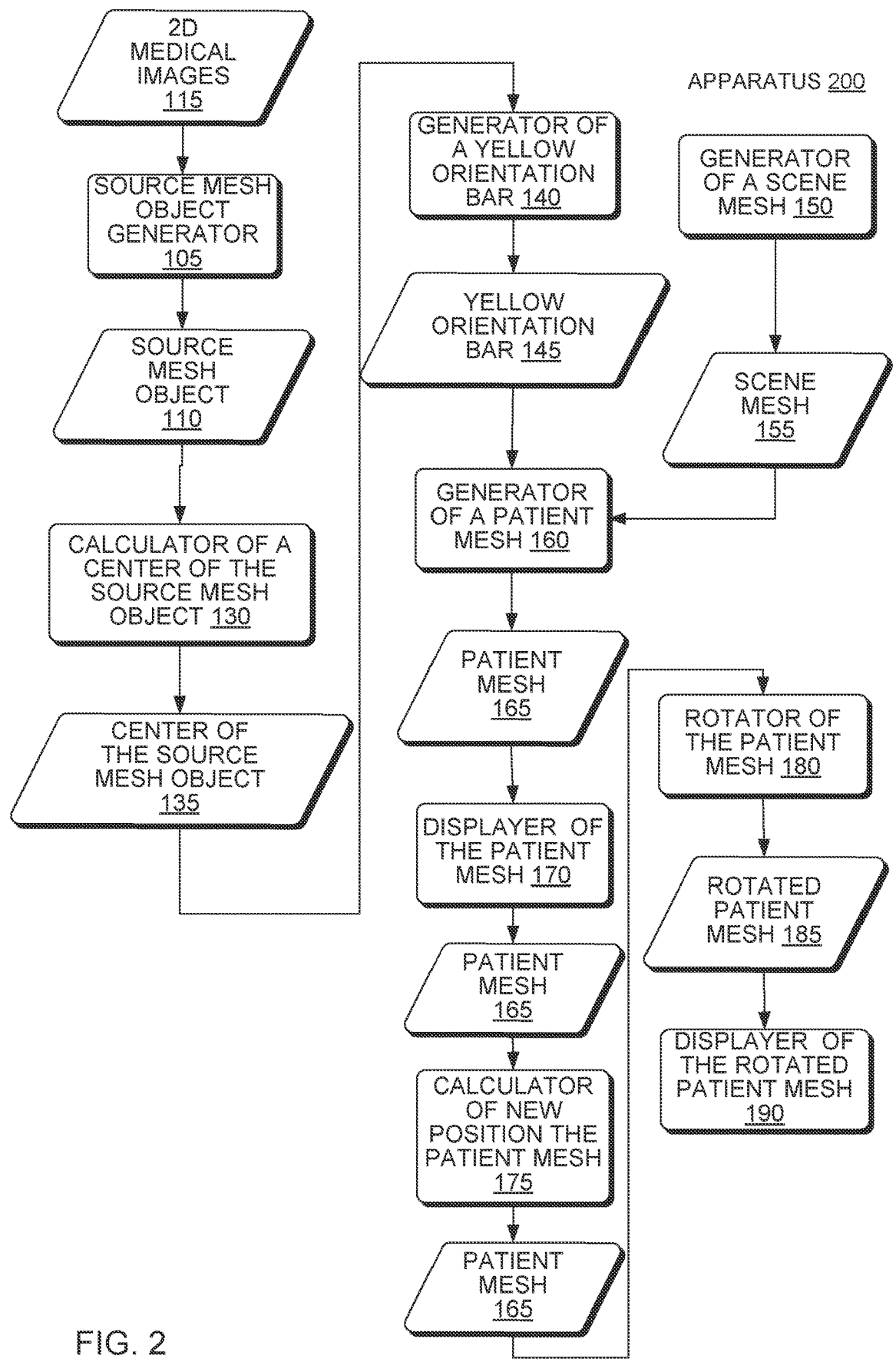
FIG. 2 is a block diagram of an apparatus of augmented reality, according to an implementation.

FIG. 2 is a block diagram of an apparatus 200 of augmented reality, according to an implementation.

The apparatus 200 includes a generator 105 of a 3D source mesh object 110 from two-dimensional (2D) or three-dimensional (3D) medical image data 115.

The apparatus 200 includes a calculator 130 of a center 135 of the 3D source mesh object 110.

Apparatus 200 also includes a generator 140 of an orientation bar 145 that is placed orthogonally in the center of the 3D source mesh object 110. In some implementations, such as shown in FIG. 4, the orientation bar is yellow colored and about 1 cm in length. In other implementations the orientation bar is between 10 cm and 1 meter in length. In other implementations, the color of the orientation bar is a color other than yellow Apparatus 200 also includes a generator 150 of a scene mesh object 155. In some implementations, the examination room is scanned by a mixed reality smartglass, such as the Microsoft HoloLens® device, to obtain the scene mesh object 155. In some implementations, the scene mesh object 155 is a Game Object in Unity, which the Scene Understanding software development toolkit transforms unstructured environment data from the room scan and converts the unstructured environment data in the room scan into an abstract representation. One example of the scene mesh object is scene mesh object 500 in FIG. 5.

Thereafter, in some implementations the operator initiates the placement calculations, such as by pressing a relevant button with their left index finger, while manually placing their right index fingertip on the center location that was marked in step 1725 on the patient body. Alternatively, can use pinch and hold just with the right index and thumb finger to initiate the operator.

Apparatus 200 includes a generator 160 of a patient mesh object 165 that cuts the scene mesh object 155 in reference to original dimensions of the 3D source mesh object (by placing the 3D source mesh object downwards by half the depth of the 3D source mesh object respective to each axis and the orientation of the patient), the initial orientation of the human from the operator, the original size from the 3D source mesh object, and the location marked by the operator's right index fingertip. One example of the patient mesh object 165 is patient mesh object 600 in FIG. 6.

Apparatus 200 includes a displayer 170 of the patient mesh object 165. The displayed patient mesh object 165 includes the yellow orientation bar 145.

Apparatus 200 includes a calculator 175 of a new position of the patient mesh object 165 in terms of x, y and z coordinates.

Apparatus 200 includes a rotator 180 of the patient mesh object 165, yielding a rotated patient mesh object 185. The patient mesh object 165 is rotated in reference to two points, the rightmost and the leftmost points from the patient mesh object 165.

Apparatus 200 includes a displayer 190 of the rotated patient mesh object 185. The displayed patient mesh object includes the yellow orientation bar 145.

Apparatus 200 can be implemented as a component of a mixed reality smartglass, such as the Microsoft Hololens®, or another device such as the Microsoft Kinect® device.

Figure 3:
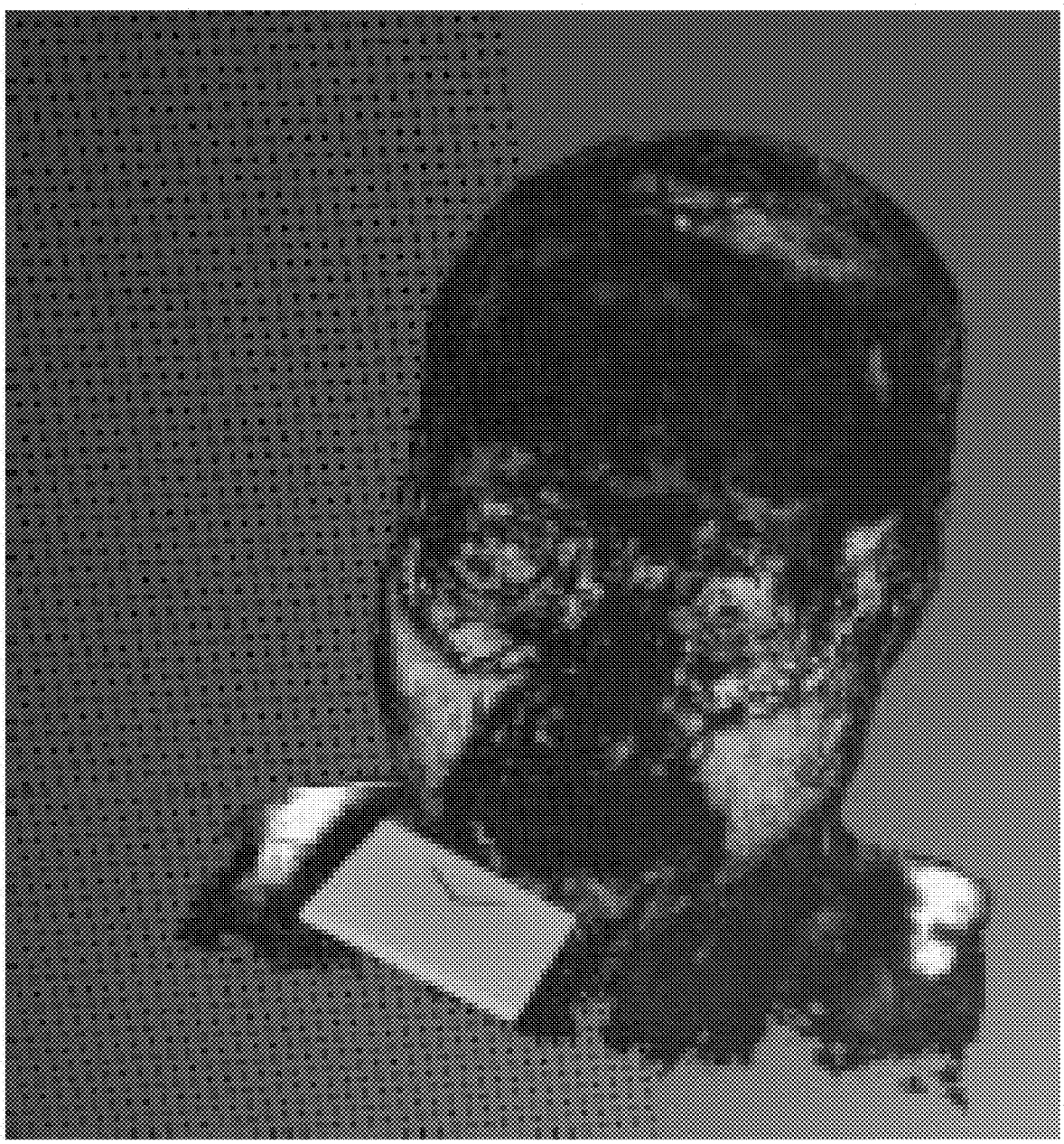
FIG. 3 is a visual depiction of a 3D source mesh object, according to an implementation.

FIG. 3 is a visual depiction of a 3D source mesh object 300, according to an implementation. 3D source mesh object 300 is one example of the 3D source mesh object 114 object in FIG. 1.

FIG. 4 is a visual depiction of a yellow orientation bar 400, according to an implementation. The yellow orientation bar 400 is one example of the yellow orientation bar 145 in FIG. 1.

Figure 5:
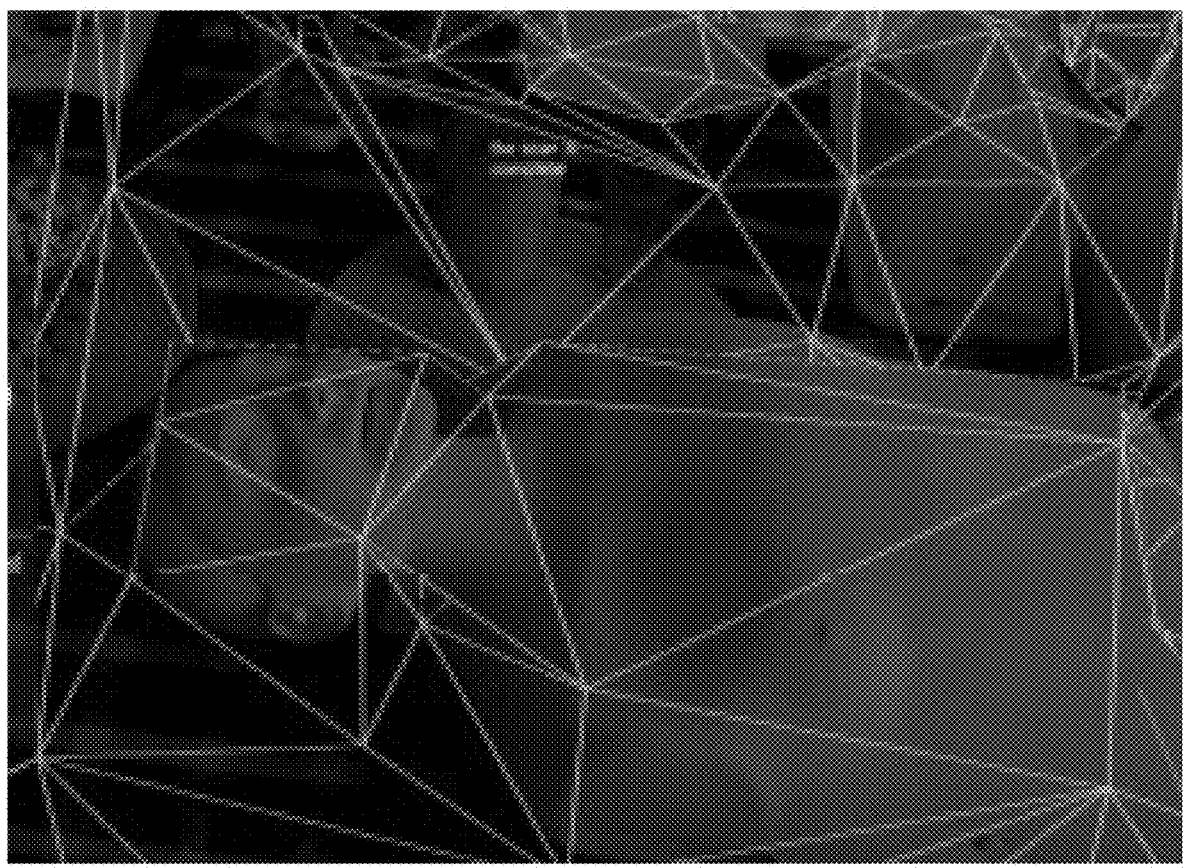
FIG. 5 is a visual depiction of a scene mesh object, according to an implementation.

FIG. 5 is a visual depiction of a scene mesh object 500, according to an implementation. The scene mesh object 500 is one example of the scene mesh object 155 in FIG. 1.

Figure 6:
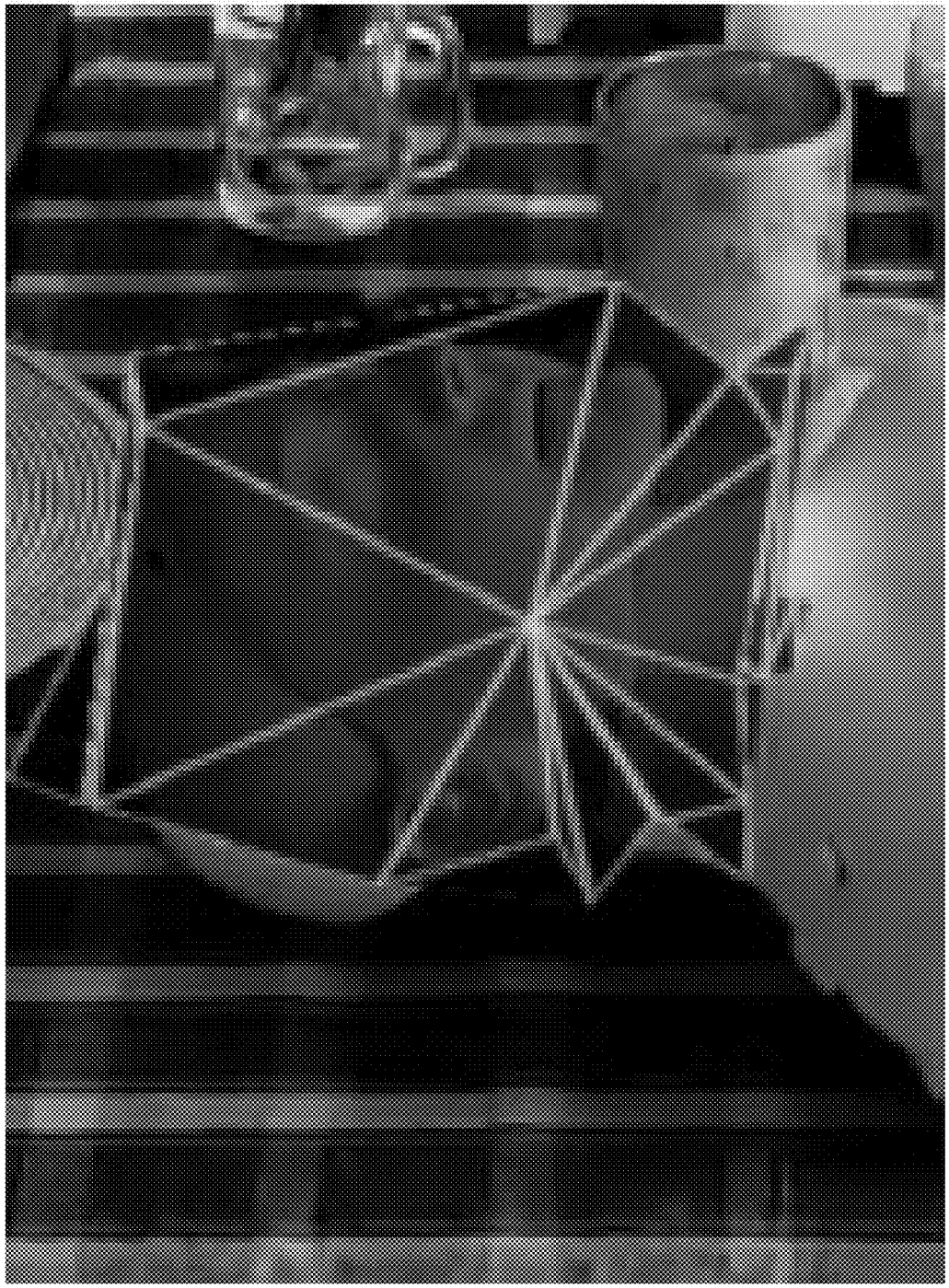
FIG. 6 is a visual depiction of a patient mesh object according to an implementation.

FIG. 6 is a visual depiction of a patient mesh object 600 according to an implementation. The patient mesh object 600 is one example of the patient mesh object 185 in FIG. 1.

Figure 7:
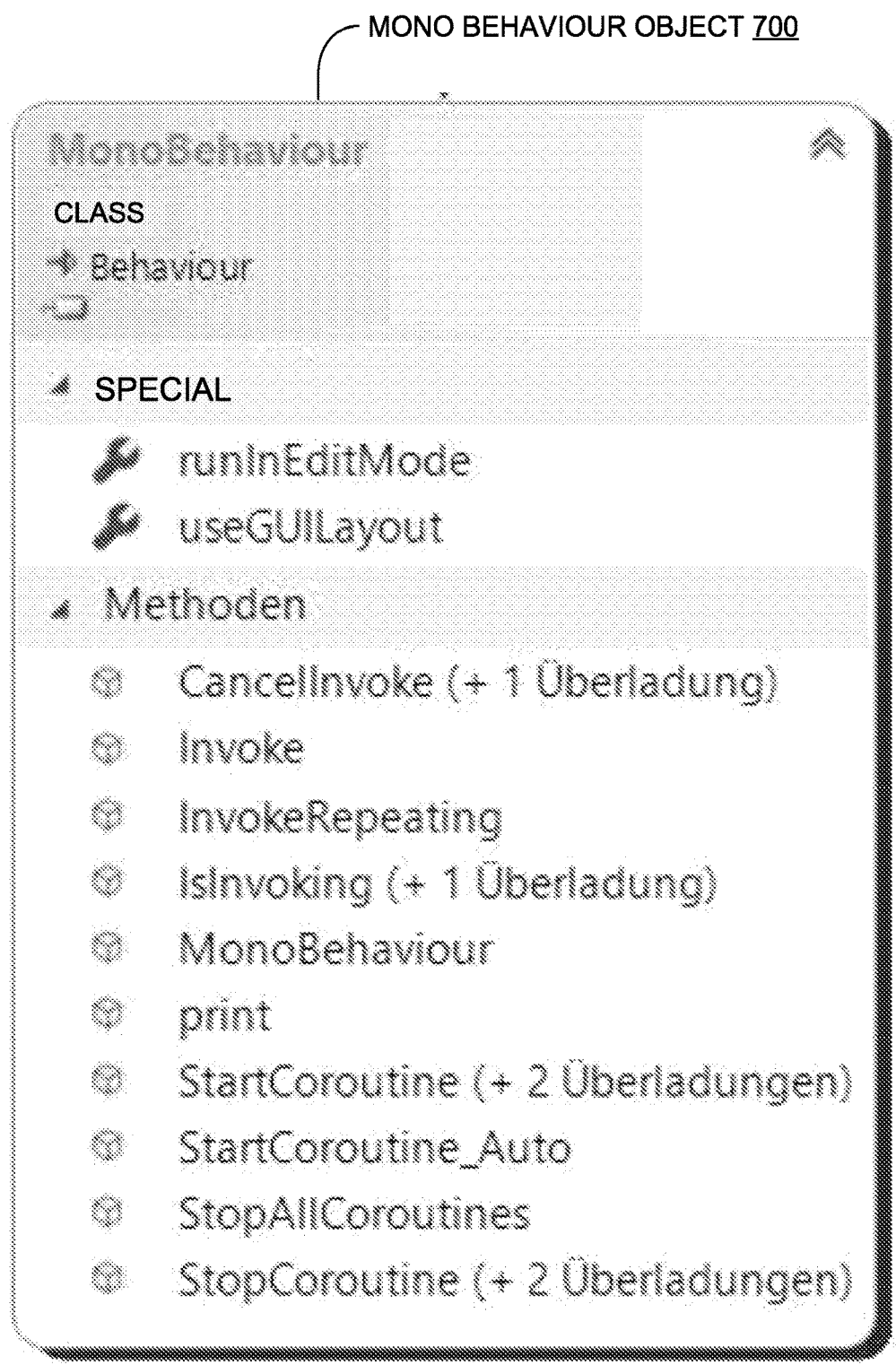
FIG. 7 is a diagram of a mono behavior placement engine object, according to an implementation.

FIG. 7 is a diagram of a mono behavior placement engine object 700, according to an implementation. The mono behavior placement engine object 700 is instantiated from a mono behavior placement engine class, which is the base class from which every Unity script derives. The objects in FIG. 8-16 are instantiated from classes that explicitly derive from the mono behavior placement engine class.

Figure 8:
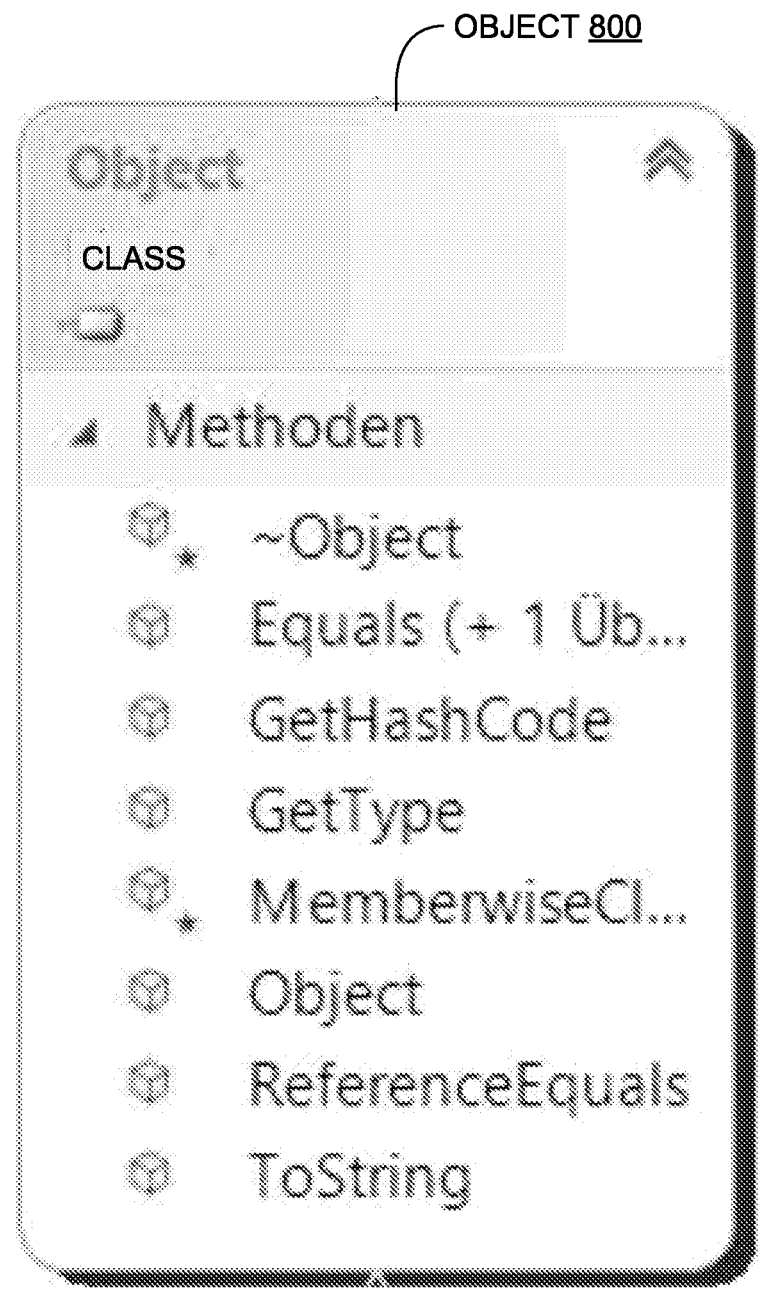
FIG. 8 is a diagram of an object, according to an implementation.

FIG. 8 is a diagram of a base object 800, according to an implementation. The base object is instantiated from a base class of all objects Unity can reference. All public data in an object that derives from the base object is shown in the inspector as a drop target, allowing the value to be set from a graphical user interface. UnityEngine.Object is the base class of all built-in Unity objects.

Figure 9:
FIG. 9 is a diagram of a feature object, according to an implementation.

FIG. 9 is a diagram of a feature object 900, according to an implementation. The feature object 900 is instantiated from the base class in FIG. 8 for every feature, such as placement, showing medical object etc., in an application for designing new features and describes the behavior how to use them from other scripts.

Figure 10:
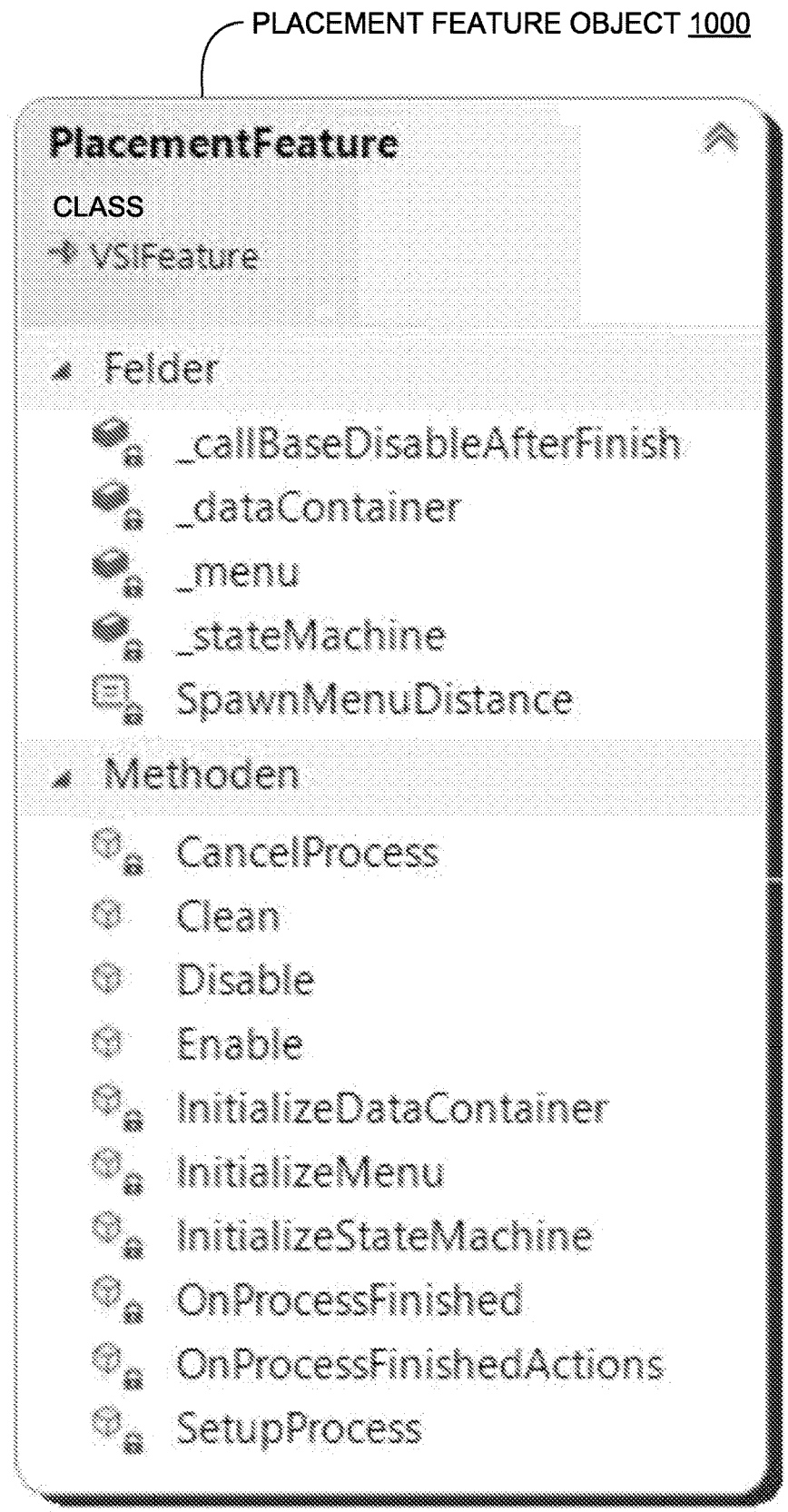
FIG. 10 is a diagram of a placement feature object, according to an implementation.

FIG. 10 is a diagram of a placement feature object 1000, according to an implementation. The placement feature object 1000 is instantiated from a placement feature class that is a derived feature class for the placement feature for handling all the communication between the user interface and a logical part of the feature.

Figure 11:
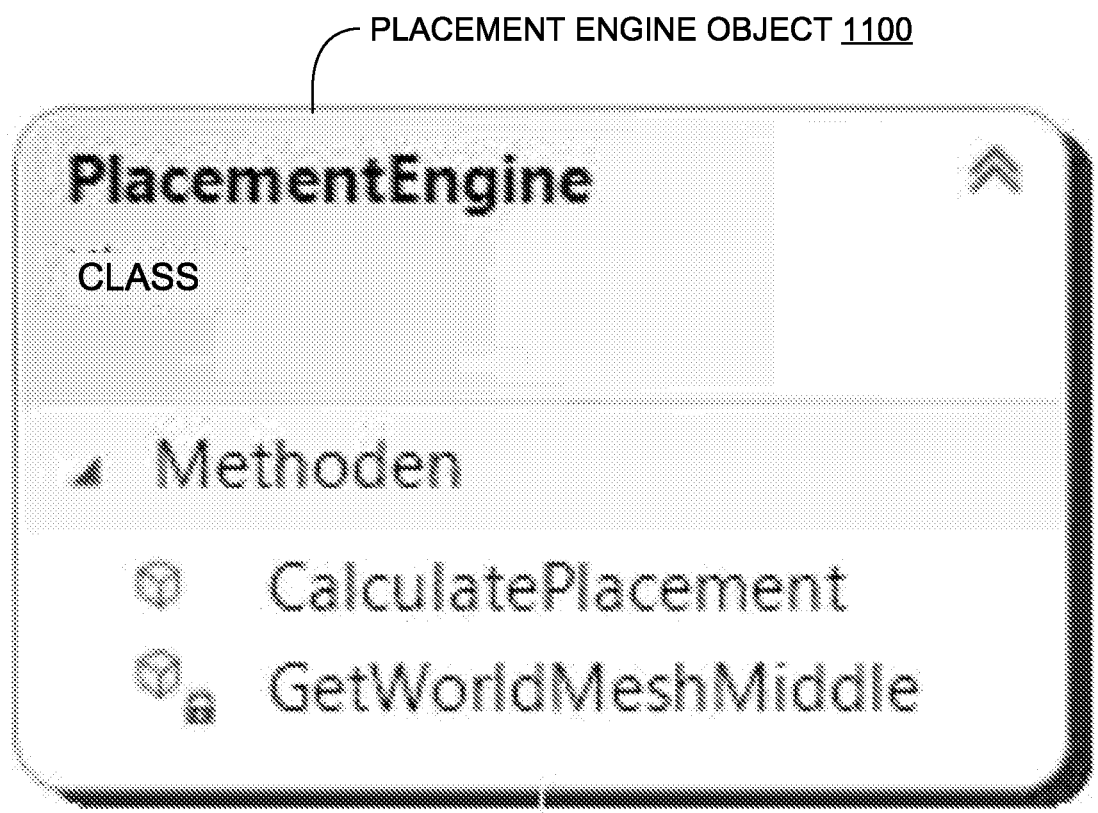
FIG. 11 is a diagram of a placement engine object, according to an implementation.

FIG. 11 is a diagram of a placement engine object 1100, according to an implementation. The placement engine object 1100 calculates the position for the 3D source mesh object and calculate the center of the patient mesh object.

Figure 12:
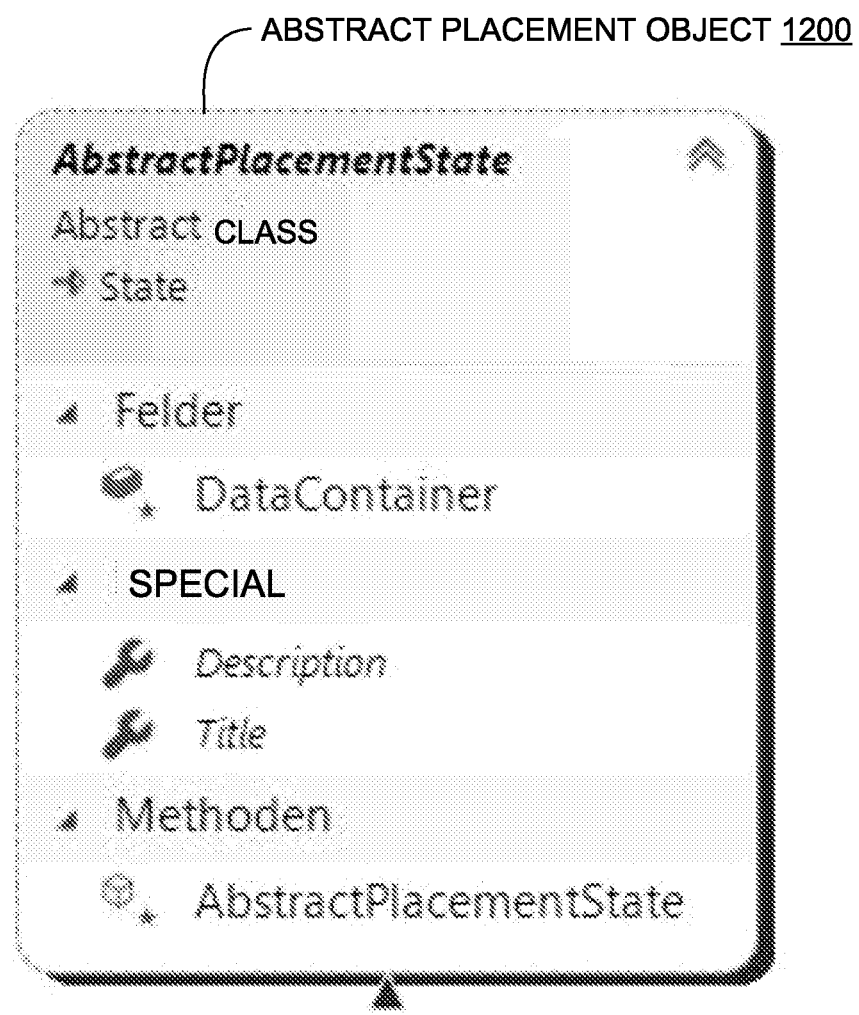
FIG. 12 is a diagram of an abstract placement object, according to an implementation.

FIG. 12 is a diagram of an abstract placement object 1200, according to an implementation. The abstract placement object 1200 is instantiated from a abstract placement class, that is derived from a state class for the placement feature. The abstract placement object 1200 contains only the title, description and a data container of the feature.

Figure 13:
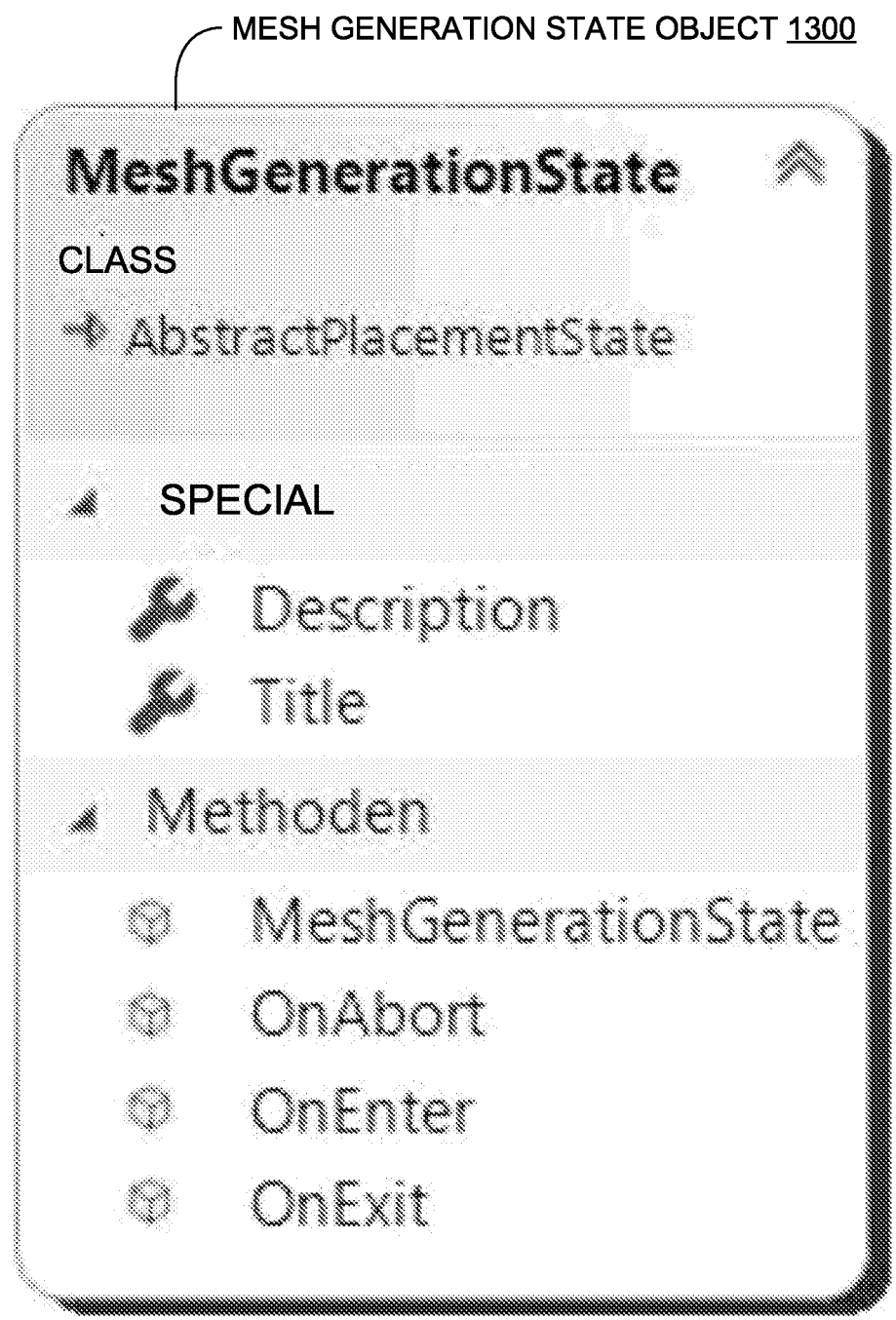
FIG. 13 is a diagram of a mesh object generation state object, according to an implementation.

FIG. 13 is a diagram of a mesh generation state object 1300, according to an implementation. The mesh generation state object 1300 is instantiated from a mesh generation state class, that is derived from the state class for the patient mesh generation. The mesh generation state object 1300 contains only the title and description of the feature for the user interface.

Figure 14:
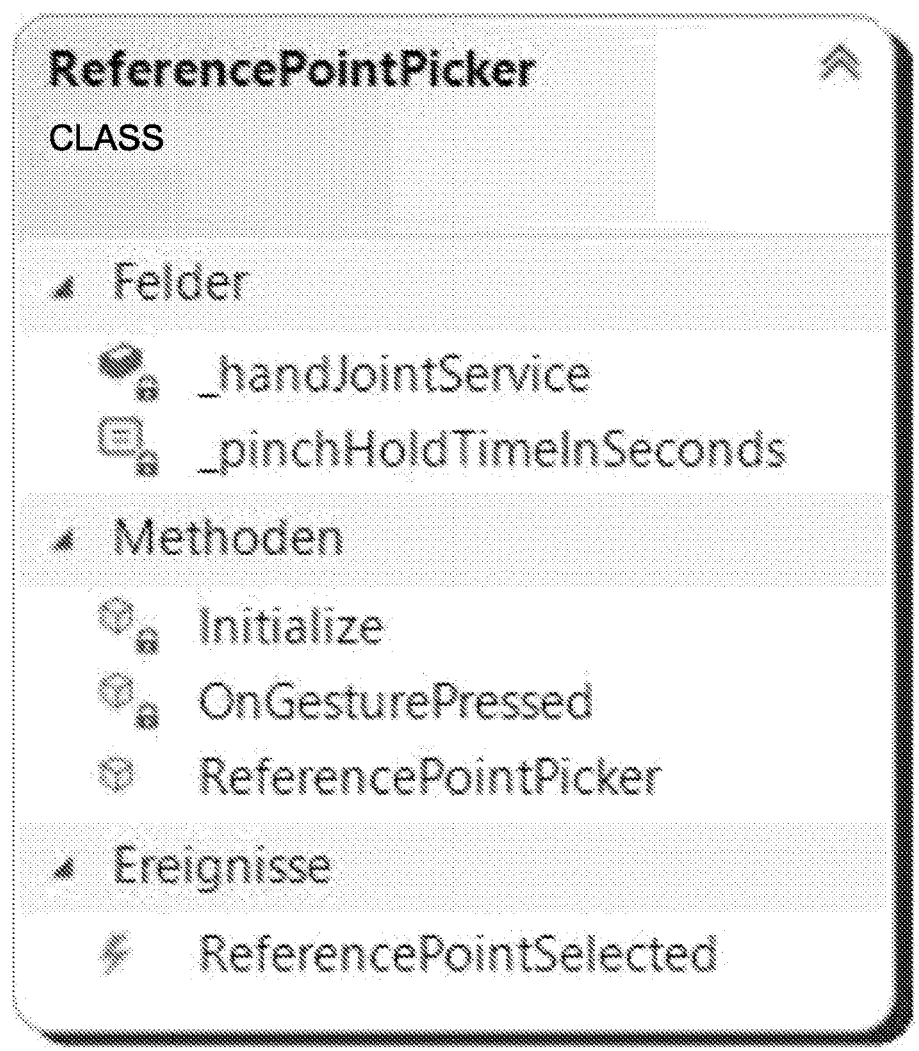
FIG. 14 is a diagram of reference point picker object, according to an implementation.

FIG. 14 is a diagram of reference point picker object 1400, according to an implementation. The reference point picker object 1400 is instantiated from a reference point picker class and manages gesture recognition and finger tracking.

Figure 15:
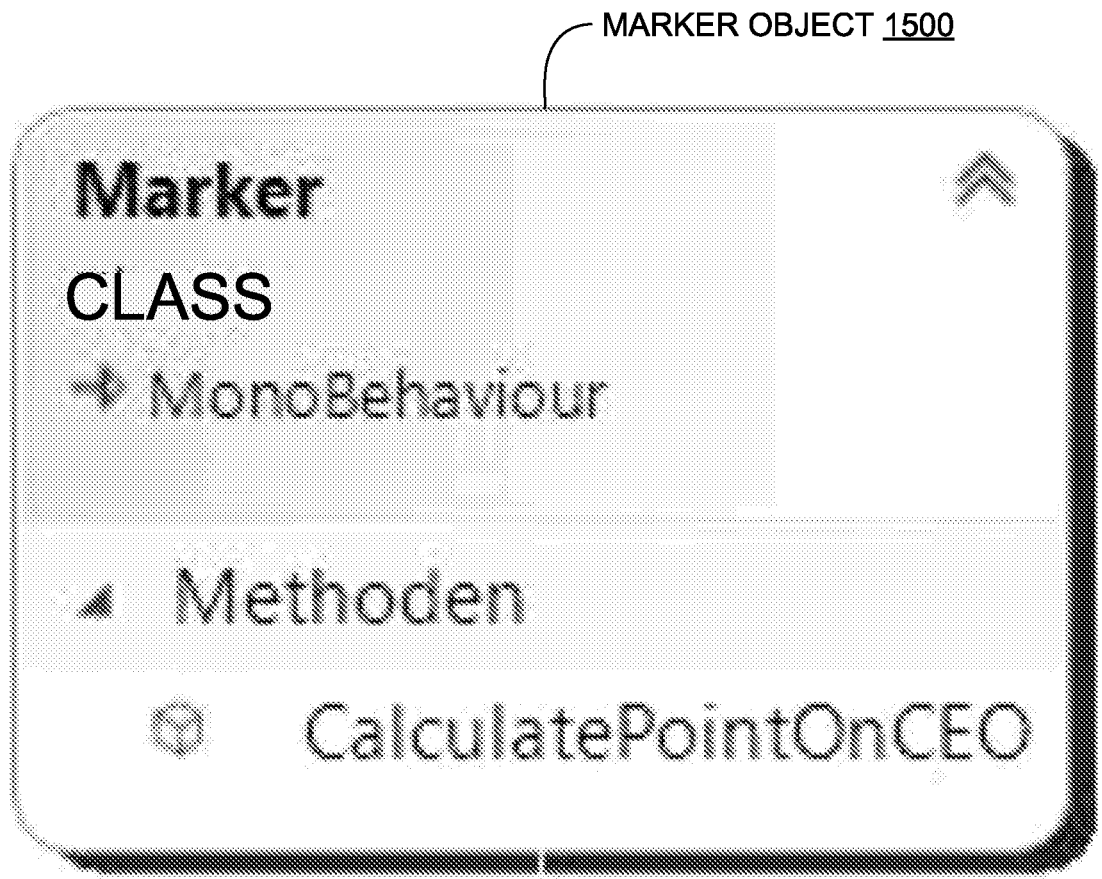
FIG. 15 is a diagram of a marker object, according to an implementation.

FIG. 15 is a diagram of a marker object 1500, according to an implementation. The marker object 1500 is instantiated from a marker class. The marker object 1500 calculates the yellow orientation bar on the 3D source mesh object.

Figure 16:
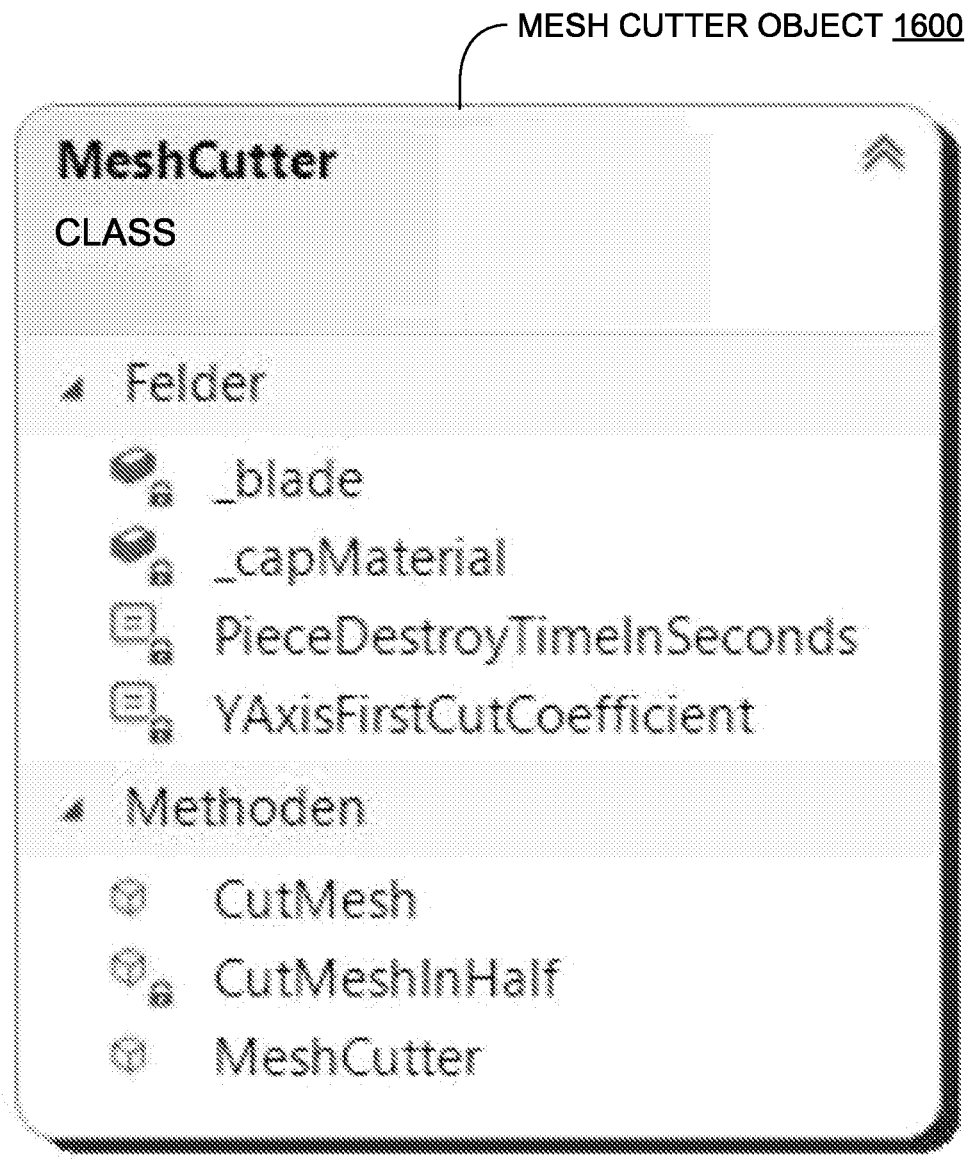
FIG. 16 is a diagram of a mesh object cutter object, according to an implementation.

FIG. 16 is a diagram of a mesh object cutter object 1600, according to an implementation. The mesh object cutter object 1600 is instantiated from a mesh object cutter class. The mesh object cutter object 1600 performs correct cutting of the scene mesh object to generate the patient mesh object is placed here.

Method Implementations

In the previous section, apparatus of the operation of an implementation was described. In this section, the particular methods performed by the mixed reality smartglass of such an implementation are described by reference to a series of flowcharts.

Figure 17:
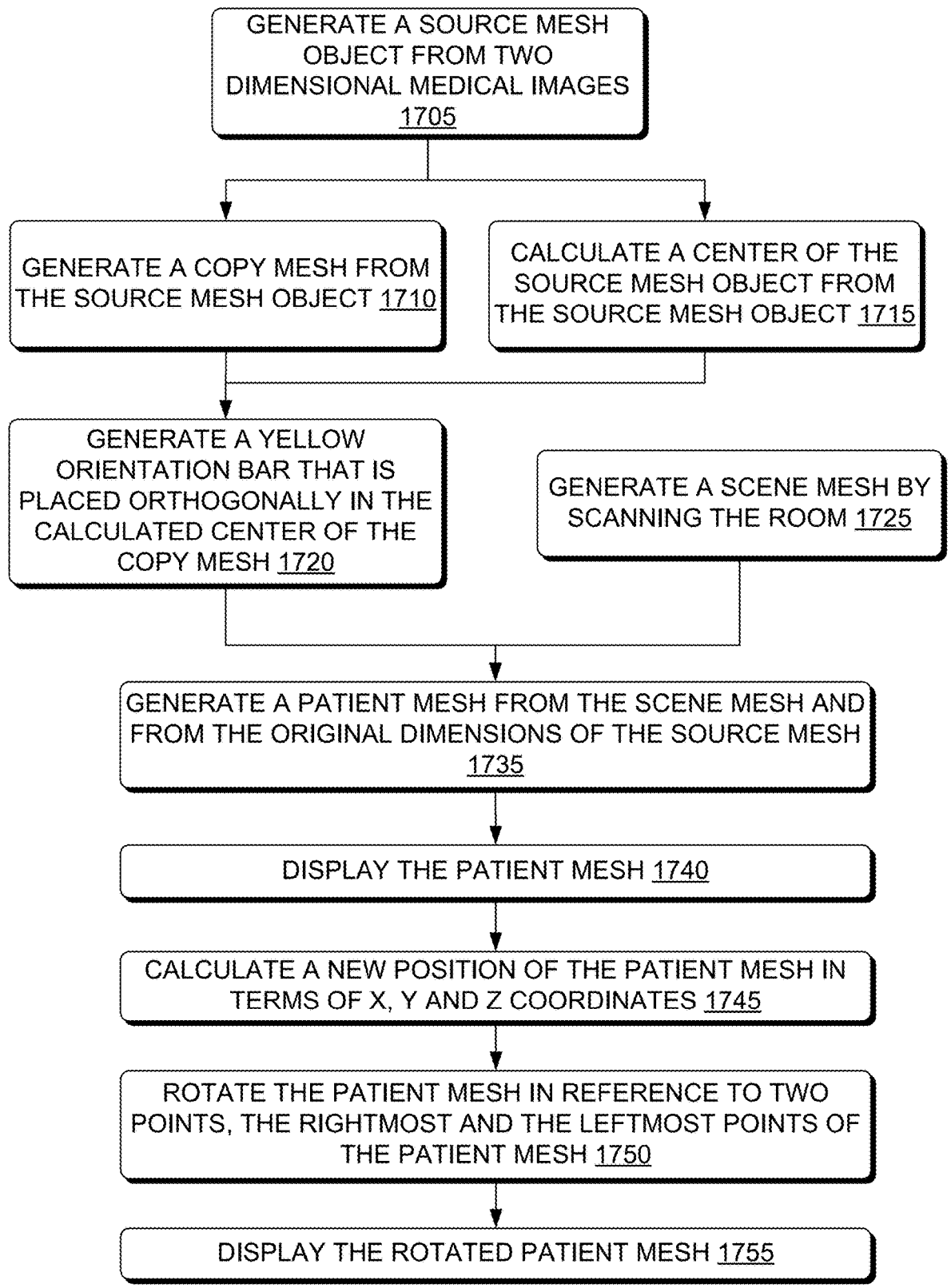
FIG. 17 is a flowchart of a method of augmented reality, according to an implementation.

FIG. 17 is a flowchart of a method 1700 of augmented reality, according to an implementation.

The method 1700 includes generating a 3D source mesh object from two-dimensional (2D) or three-dimensional (3D) medical image data, at block 1705.

In some implementations of block 1705, the 3D source mesh object is generated by a three-dimensional engine (such as the Unity® 3D engine) from the medical images, in which case the 3D source mesh object is a Game Object in Unity, the Game Object being a fundamental object that represents characters, props and scenery, and which acts as a container for components which define behavior and implement functionality. In some implementations, the 3D source mesh object is encoded in a byte format.

Thereafter, in some implementations, the method includes generating a copy mesh object by copying the 3D source mesh object, at block 1710.

Thereafter, the method 1700 includes calculating a center of the 3D source mesh object from the 3D source mesh object, at block 1715.

Thereafter, the method 1700 includes generating a yellow orientation bar of between 10 cm and 1 meter that is placed orthogonally in the center of the copy mesh object, at block 1720.

The method 1700 also includes generating a scene mesh object by scanning the room, at block 1725. In some implementations, the scene mesh object is a Game Object in Unity, created by the Scene Understanding software development toolkit which transforms unstructured environment data from the room scan and converts the unstructured environment data into an abstract representation.

Thereafter, in some implementations the operator initiates the placement calculations, such as by pressing a relevant button with their left index finger, while manually placing their right index fingertip on the center location that was marked in step 1725 on the patient body. Method 1700 includes generating a patient mesh object, at block 1735, by cutting the scene mesh object in reference to original dimensions of the 3D source mesh object (by placing the 3D source mesh object downwards by half the depth of the 3D source mesh object respective to each axis and the orientation of the patient), the initial orientation of the human from the operator, the original size from the 3D source mesh object, and the location marked by the operator's right index fingertip.

Thereafter, the patient mesh object is displayed, at block 1740. The displayed patient mesh object includes the yellow orientation bar.

Thereafter, a new position of the patient mesh object in terms of x, y and z coordinates is calculated, at block 1745.

Thereafter, the patient mesh object is rotated in reference to two points, the rightmost and the leftmost points from the patient mesh object, at block 1750. When the rotation is determined, thereafter, the rotated patient mesh object is displayed, at block 1755. The displayed patient mesh object includes the yellow orientation bar.

A mixed reality smartglass, such as the Microsoft Hololens®, or another device such as the Microsoft Kinect® device, performs method 1700.

Figure 18:
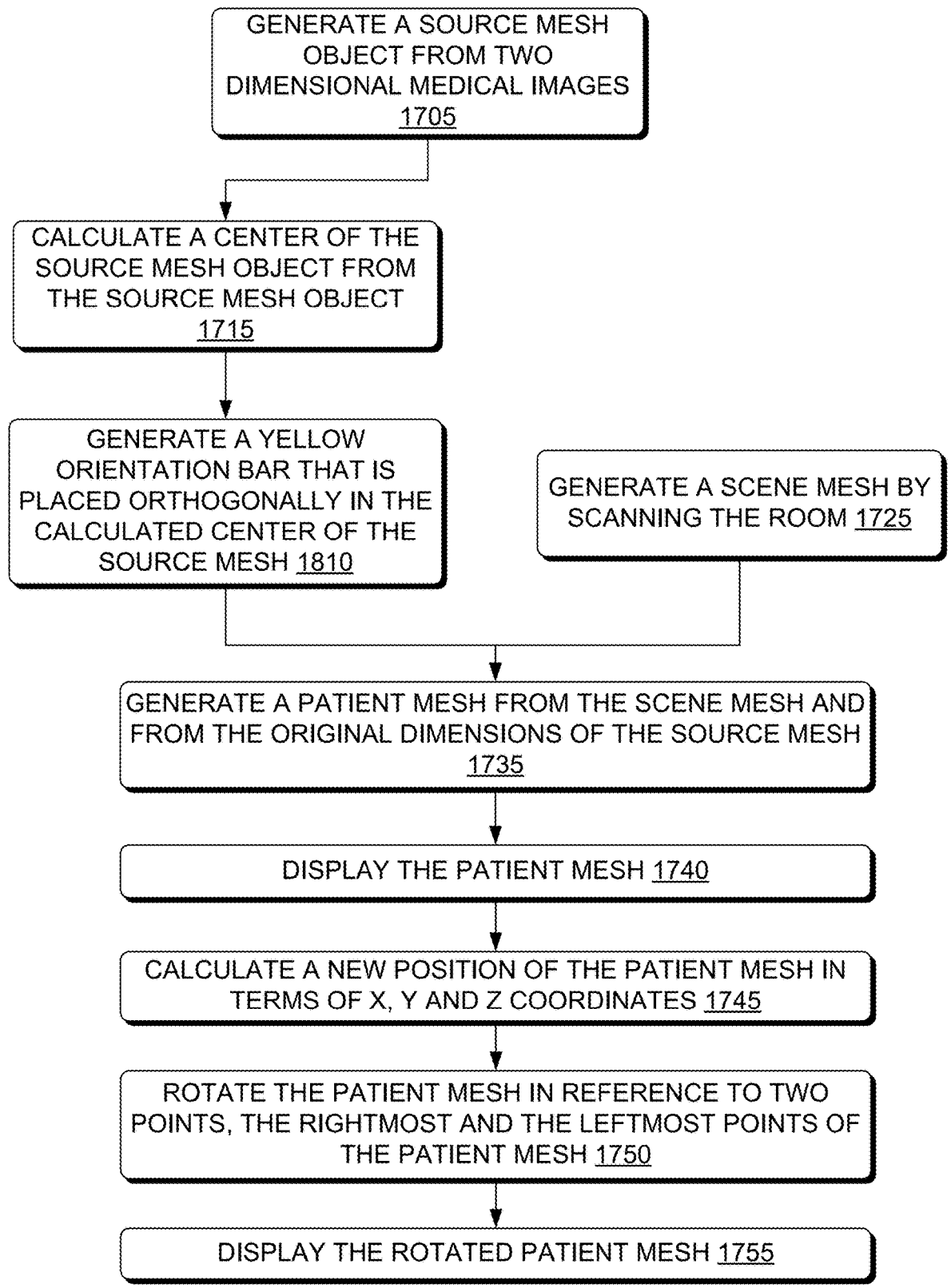
FIG. 18 is a flowchart of a method of augmented reality, according to an implementation.

FIG. 18 is a flowchart of a method 1800 of augmented reality, according to an implementation.

The method 1800 includes generating a 3D source mesh object from two-dimensional (2D) or three-dimensional (3D) medical image data, at block 1705.

In some implementations of block 1705, the 3D source mesh object is generated by a three-dimensional engine (such as the Unity® 3D engine) from the medical images, in which case the 3D source mesh object is a Game Object in Unity, the Game Object being a fundamental object that represents characters, props and scenery, and which acts as a container for components which define behavior and implement functionality. In some implementations, the 3D source mesh object is encoded in a byte format.

Thereafter, the method 1700 includes calculating a center of the 3D source mesh object from the 3D source mesh object, at block 1715.

Thereafter, the method 1700 includes generating a yellow orientation bar of about 1 cm that is placed orthogonally in the center of the 3D source mesh object, at block 1810.

The method 1700 also includes generating a scene mesh object by scanning the room, at block 1725. In some implementations, the scene mesh object is a Game Object in Unity, created by the Scene Understanding software development toolkit which transforms unstructured environment data from the room scan and converts the unstructured environment data into an abstract representation.

Thereafter, in some implementations the operator initiates the placement calculations, such as by pressing a relevant button with their left index finger, while manually placing their right index fingertip on the center location that was marked in step 1725 on the patient body. Method 1700 includes generating a patient mesh object, at block 1735, by cutting the scene mesh object in reference to original dimensions of the 3D source mesh object (by placing the 3D source mesh object downwards by half the depth of the 3D source mesh object respective to each axis and the orientation of the patient), the initial orientation of the human from the operator, the original size from the 3D source mesh object, and the location marked by the operator's right index fingertip. Alternatively, can use pinch and hold just with the right index and thumb finger to initiate the operator.

Thereafter, the patient mesh object is displayed, at block 1740. The displayed patient mesh object includes the yellow orientation bar.

Thereafter, a new position of the patient mesh object in terms of x, y and z coordinates is calculated, at block 1745.

Thereafter, the patient mesh object is rotated in reference to two points, the rightmost and the leftmost points from the patient mesh object, at block 1750. When the rotation is determined, thereafter, the rotated patient mesh object is displayed, at block 1755. The displayed patient mesh object includes the yellow orientation bar.

A mixed reality smartglass, such as the Microsoft Hololens®, or another device such as the Microsoft Kinect® device, performs method 1700.

Hardware and Operating Environments

Figure 19:
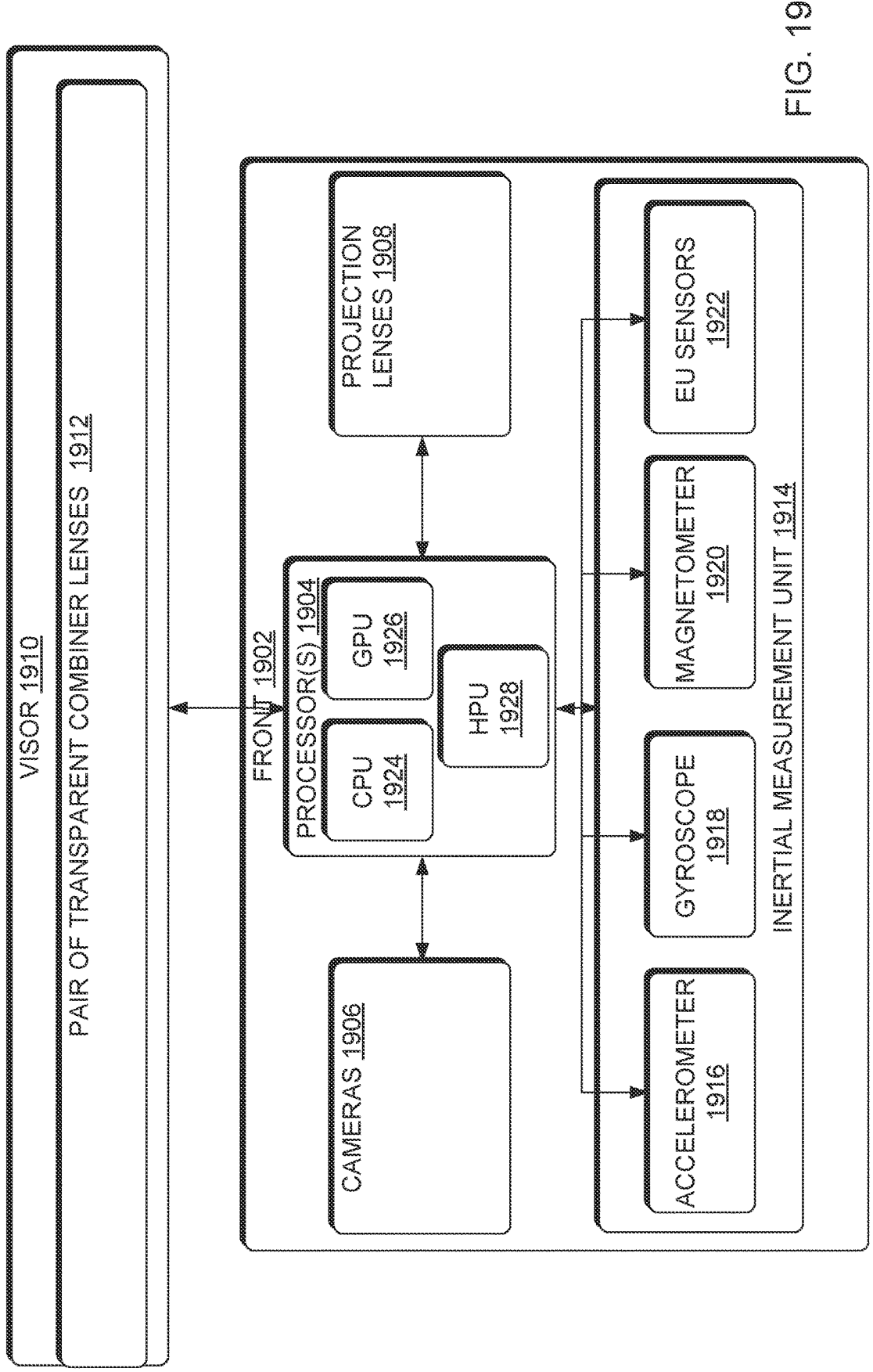
FIG. 19 is a block diagram of a mixed reality smartglass that calculates position and rotation from a manually set reference point in a spatial mesh object, according to an implementation.

FIG. 19 is a block diagram of a mixed reality smartglass 1900 that calculates position and rotation from a manually set reference point in a spatial mesh object, according to an implementation. The mixed reality smartglass 1900 can include the apparatus 100 in FIG. 1, apparatus 200 in FIG. 2, the objects in FIGS. 7-16 and/or can perform the methods 1700 in FIGS. 17 and 1800 in FIG. 18. The mixed reality smartglass 1900 is a head-mounted display unit and in some implementation is connected to an adjustable, cushioned inner headband, which can tilt the mixed reality smartglass 1900 up and down, as well as forward and backward. To wear the unit, the user can fit the mixed reality smartglass 1900 on their head, using an adjustment wheel at the back of the headband to secure the mixed reality smartglass 1900 around the crown, supporting and distributing the weight of the mixed reality smartglass 1900 equally for comfort, before tilting the visor towards the front of the eyes.

In some implementations, the front 1902 of the unit houses many of the sensors and related hardware, including the processors 1904, cameras 1906 and projection lenses 1908. In some implementations, the visor 1910 is tinted; enclosed in the visor 1910 is a pair of transparent combiner lenses 1912, in which the projected images are displayed in the lower half. In some implementations, the mixed reality smartglass 1900 must be calibrated to the interpupillary distance (IPD), or accustomed vision of the user.

In some implementations, along the bottom edges of the side, located near the user's ears, are a pair of small, 3D audio speakers. The speakers, competing against typical sound systems, do not obstruct external sounds, allowing the user to hear virtual sounds, along with the environment. Using head-related transfer functions, the mixed reality smartglass 1900 generates binaural audio, which can simulate spatial effects; meaning the user, virtually, can perceive and locate a sound, as though it is coming from a virtual pinpoint or location.

In some implementations, on the top edge are two pairs of buttons: display brightness buttons above the left ear, and volume buttons above the right ear. Adjacent buttons are shaped differently—one concave, one convex—so that the user can distinguish them by touch.

The mixed reality smartglass 1900 includes an inertial measurement unit (IMU) 1914 (which includes an accelerometer 1916, a gyroscope 1918, and a magnetometer 1920) four "environment understanding" (EU) sensors 1922 (two on each side), and in some implementations, an energy-efficient depth camera with a 120°×120° angle of view, a 2.4-megapixel photographic video camera, a four-microphone array, and an ambient light sensor.

In some implementations, SoC contains a CPU 1924 and a GPU 1926. In some implementations, the mixed reality smartglass 1900 features a custom-made holographic processing unit (HPU) 1928, a coprocessor manufactured specifically for the mixed reality smartglass 1900. In some implementations, the SoC and the HPU 1928 each have 1 GB LPDDR3 and share 8 MB SRAM, with the SoC also controlling 64 GB eMMC and running an operating system. In some implementations, the HPU 1928 uses 28 custom DSPs from Tensilica to process and integrates data from the sensors, as well as handling tasks such as spatial mapping, gesture recognition, and voice and speech recognition. In some implementations, the HPU 1928 processes "terabytes of information." The display field of view can be 30°×17.5°. The HPU 2000 in FIG. 20 is one example of the HPU 1928.

The mixed reality smartglass 1900 can include IEEE 802.11ac Wi-Fi and Bluetooth 4.1 Low Energy (LE) wireless connectivity. The headset can use Bluetooth LE to pair with the included Clicker, a thumb-sized finger-operating input device that can be used for interface scrolling and selecting. The Clicker features a clickable surface for selecting, and an orientation sensor which provides for scrolling functions via tilting and panning of the unit. The Clicker features an elastic finger loop for holding the device, and a USB 2.0 micro-B receptacle for charging its internal battery.

Figure 20:
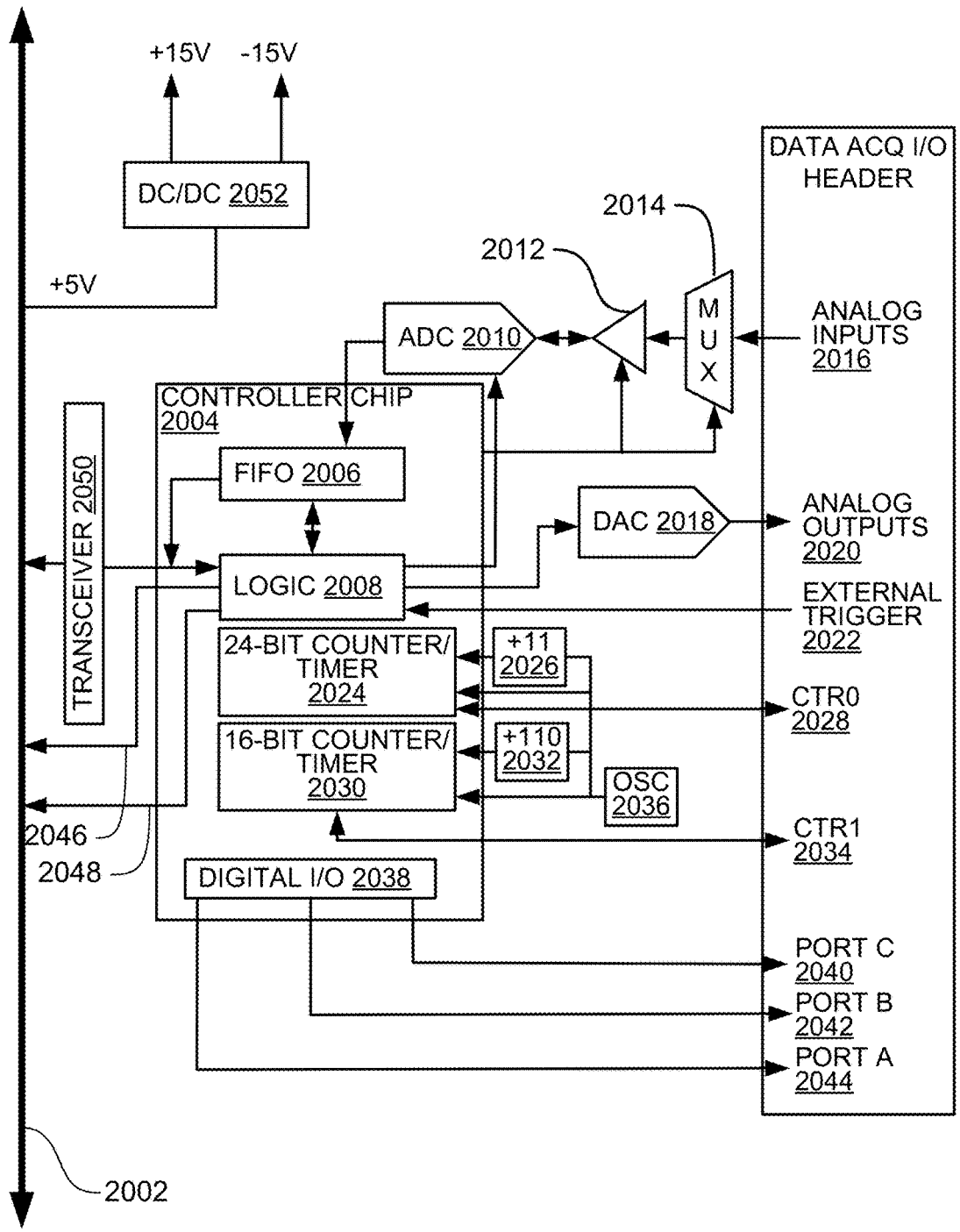
FIG. 20 is a block diagram of a holographic processing unit of a mixed reality smartglass, according to an implementation.

FIG. 20 is a block diagram of a holographic processing unit 2000 of a mixed reality smartglass, according to an implementation. The holographic processing unit (HPU) 2000 is one example of the HPU 4712 in FIG. 19 above. Some implementations of the HPU 2000 provide 16-bit A/D performance with input voltage capability up to +/−10V, and programmable input ranges. HPU 2000 is one example of HPU 1928 in FIG. 1928.

The HPU 2000 can include a bus 2002, such as a conventional PC/104 bus. The HPU 2000 can be operably coupled to a controller chip 2004. Some implementations of the controller chip 2004 include an analog/digital first-in/first-out (FIFO) buffer 2006 that is operably coupled to controller logic 2008. In some implementations of the HPU 2000, the FIFO 2006 receives signal data from and analog/digital converter (ADC) 2010, which exchanges signal data with a programmable gain amplifier 2012, which receives data from a multiplexer 2014, which receives signal data from analog inputs 2016.

In some implementations of the HPU 2000, the controller logic 2008 sends signal data to the ADC 2010 and a digital/analog converter (DAC) 2018. The DAC 2018 sends signal data to analog outputs. The analog outputs, after proper amplification, can be used to modulate coolant valve actuator positions. In some implementations of the HPU 2000, the controller logic 2008 receives signal data from an external trigger 2022.

In some implementations of the HPU 2000, the controller chip 2004 includes a digital input/output (I/O) component 2038 that sends digital signal data to computer output ports.

In some implementations of the HPU 2000, the controller logic 2008 sends signal data to the bus 2002 via a control line 2046 and an interrupt line 2048. In some implementations of the HPU 2000, the controller logic 2008 exchanges signal data to the bus 2002 via a transceiver 2050.

Some implementations of the HPU 2000 include 12-bit D/A channels, programmable digital I/O lines, and programmable counter/timers. Analog circuitry can be placed away from the high-speed digital logic to ensure low-noise performance for important applications. Some implementations of the HPU 2000 are fully supported by operating systems that can include, but are not limited to, DOS™, Linux™, RTLinux™, QNX™, Windows 98/NT/2000/XP/CE™, Forth™, and VxWorks™ to simplify application development.

Figure 21:
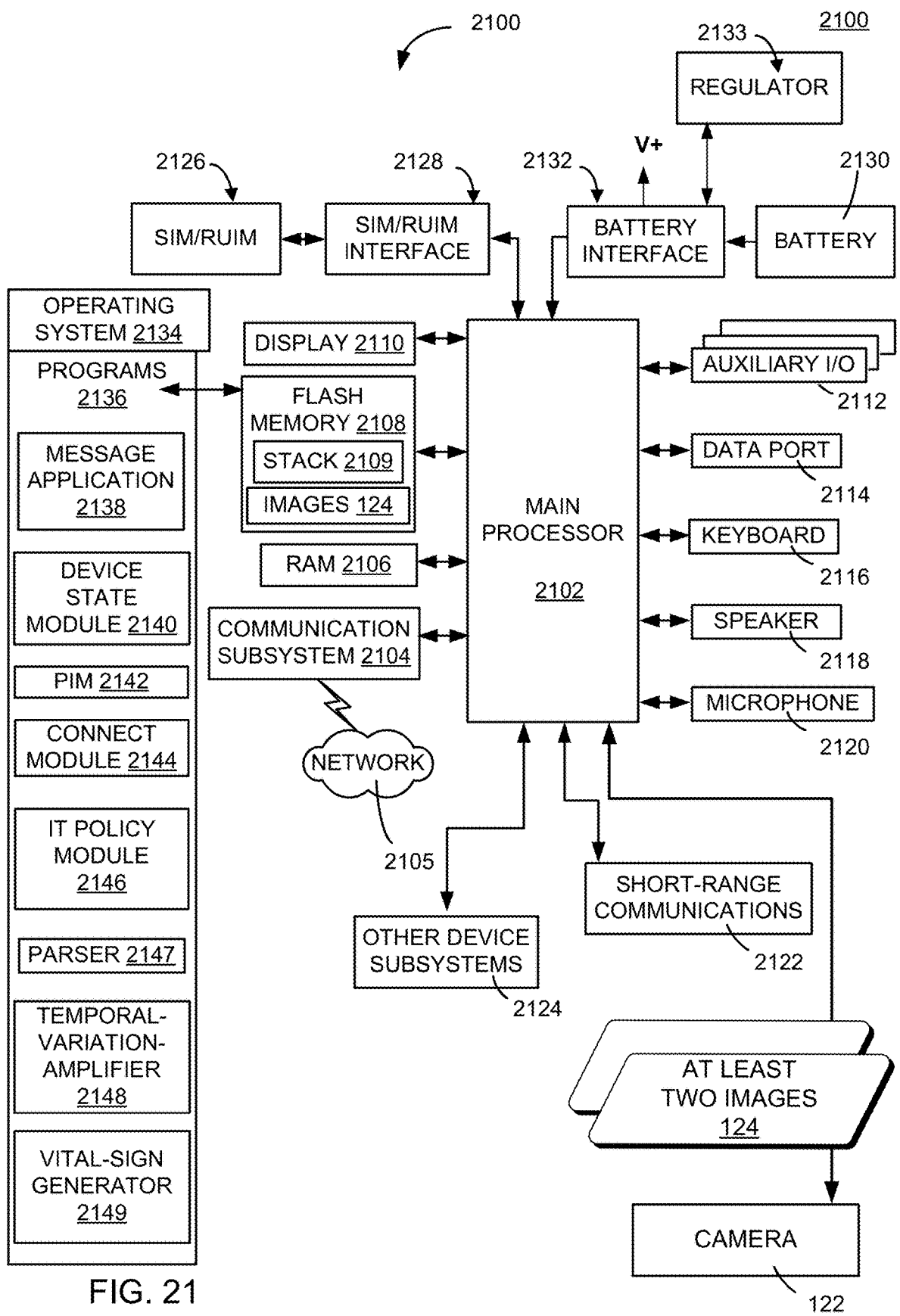
FIG. 21 is a block diagram of a hardware and operating environment in which different implementations can be practiced.

FIG. 21 is a block diagram of a hardware and operating environment 2100 in which different implementations can be practiced. The description of FIG. 21 provides an overview of computer hardware and a suitable computing environment in conjunction with which some implementations can be implemented. Implementations are described in terms of a computer executing computer-executable instructions. However, some implementations can be implemented entirely in computer hardware in which the computer-executable instructions are implemented in read-only memory. Some implementations can also be implemented in client/server computing environments where remote devices that perform tasks are linked through a communications network. Program modules can be located in both local and remote memory storage devices in a distributed computing environment.

Computer 2102 includes a processor 2104, commercially available from Intel, Motorola, Cyrix and others. Computer 2102 also includes random-access memory (RAM) 2106, read-only memory (ROM) 2108, and one or more mass storage devices 2110, and a system bus 2112, that operatively couples various system components to the processing unit 2104. The memory 2106, 2108, and mass storage devices, 2110, are types of computer-accessible media. Mass storage devices 2110 are more specifically types of nonvolatile computer-accessible media and can include one or more hard disk drives, floppy disk drives, optical disk drives, and tape cartridge drives. The processor 2104 executes computer programs stored on the computer-accessible media.

Computer 2102 can be communicatively connected to the Internet 2114 via a communication device 2116. Internet 2114 connectivity is well known within the art. In one implementation, a communication device 2116 is a modem that responds to communication drivers to connect to the Internet via what is known in the art as a "dial-up connection." In another implementation, a communication device 2116 is an Ethernet® or similar hardware network card connected to a local-area network (LAN) that itself is connected to the Internet via what is known in the art as a "direct connection" (e.g., T1 line, etc.).

A user enters commands and information into the computer 2102 through input devices such as a keyboard 2118 or a pointing device 2120. The keyboard 2118 permits entry of textual information into computer 2102, as known within the art, and implementations are not limited to any particular type of keyboard. Pointing device 2120 permits the control of the screen pointer provided by a graphical user interface (GUI) of operating systems such as versions of Microsoft Windows®. Implementations are not limited to any particular pointing device 2120. Such pointing devices include mice, touch pads, trackballs, remote controls and point sticks. Other input devices (not shown) can include a microphone, joystick, game pad, satellite dish, scanner, or the like.

In some implementations, computer 2102 is operatively coupled to a display device 2122. Display device 2122 is connected to the system bus 2112. Display device 2122 permits the display of information, including computer, video and other information, for viewing by a user of the computer. Implementations are not limited to any particular display device 2122. Such display devices include cathode ray tube (CRT) displays (monitors), as well as flat panel displays such as liquid crystal displays (LCD's). In addition to a monitor, computers typically include other peripheral input/output devices such as printers (not shown). Speakers 2124 and 2126 provide audio output of signals. Speakers 2124 and 2126 are also connected to the system bus 2112.

Computer 2102 also includes an operating system (not shown) that is stored on the computer-accessible media RAM 2106, ROM 2108, and mass storage device 2110, and is and executed by the processor 2104. Examples of operating systems include Microsoft Windows®, Apple MacOS®, Linux®, UNIX®. Examples are not limited to any particular operating system, however, and the construction and use of such operating systems are well known within the art.

Implementations of computer 2102 are not limited to any type of computer 2102. In varying implementations, computer 2102 comprises a PC-compatible computer, a MacOS®-compatible computer, a Linux®-compatible computer, or a UNIX®-compatible computer. The construction and operation of such computers are well known within the art.

Computer 2102 can be operated using at least one operating system to provide a graphical user interface (GUI) including a user-controllable pointer. Computer 2102 can have at least one web browser application program executing within at least one operating system, to permit users of computer 2102 to access intranet or Internet world-wide-web pages as addressed by Universal Resource Locator (URL) addresses. Examples of browser application programs include Netscape Navigator® and Microsoft Internet Explorer®.

The computer 2102 can operate in a networked environment using logical connections to one or more remote computers, such as remote computer 2128. These logical connections are achieved by a communication device coupled to, or a part of, the computer 2102. Implementations are not limited to a particular type of communications device. The remote computer 2128 can be another computer, a server, a router, a network PC, a client, a peer device or other common network node. The logical connections depicted in FIG. 21 include a local-area network (LAN) 2130 and a wide-area network (WAN) 2132. Such networking environments are commonplace in offices, enterprise-wide computer networks, intranets and the Internet.

When used in a LAN-networking environment, the computer 2102 and remote computer 2128 are connected to the local network 2130 through network interfaces or adapters 2134, which is one type of communications device 2116. Remote computer 2128 also includes a network device 2136. When used in a conventional WAN-networking environment, the computer 2102 and remote computer 2128 communicate with a WAN 2132 through modems (not shown). The modem, which can be internal or external, is connected to the system bus 2112. In a networked environment, program modules depicted relative to the computer 2102, or portions thereof, can be stored in the remote computer 2128.

Computer 2102 also includes power supply 2138. Each power supply can be a battery.

CONCLUSION

A healthcare augmented reality system is described. Although specific embodiments are illustrated and described herein, it will be appreciated by those of ordinary skill in the art that any arrangement which is calculated to achieve the same purpose may be substituted for the specific embodiments shown. This application is intended to cover any adaptations or variations. For example, although described in medical terms, one of ordinary skill in the art will appreciate that implementations can be made in dental or any other virtual reality that provides the required function.

In particular, one of skill in the art will readily appreciate that the names of the methods and apparatus are not intended to limit embodiments. Furthermore, additional methods and apparatus can be added to the components, functions can be rearranged among the components, and new components to correspond to future enhancements and physical devices used in embodiments can be introduced without departing from the scope of embodiments. One of skill in the art will readily recognize that embodiments are applicable to future imaging devices, different augmented reality devices, and new medical data storage formats.

The terminology used in this application with respect to communications is meant to include all telecommunications environments and alternate technologies which provide the same functionality as described herein.

The invention claimed is:

1. A method comprising:
generating a 3D source mesh object by a three-dimensional-augmented-reality engine from medical data, the 3D source mesh object being encoded in byte format, the medical data selected from computed tomography scan data, magnetic resonance image scan data, which is a fundamental object that represent characters, props and scenery, which acts as a container for components which define behavior and implement functionality;
generating a copy mesh object by copying the 3D source mesh object;
calculating a center of the 3D source mesh object from the 3D source mesh object;
generating a yellow orientation bar of between 1 cm and 1 meter that is placed orthogonal to the surface of the copy mesh object at the center of the copy mesh object;
generating a scene mesh object by scanning the room, the scene mesh object being a game object;
generating a patient mesh object by cutting the scene mesh object in reference to original dimensions of the 3D source mesh object by starting from a tip of a finger and placing the 3D source mesh object in a direction that is downwards by half of a depth of the 3D source mesh object.

2. A method comprising:
determining a new position of a patient mesh object in terms of x, y and z coordinates from a manually set reference point;
generating an orientation bar that is placed orthogonal to a surface of a copy mesh object at a center of the copy mesh object;
generating a scene mesh object by scanning the room, the scene mesh object being a game object; and
generating a patient mesh object by cutting the scene mesh object in reference to original dimensions of a 3D source mesh object by starting from a tip of a finger and placing the 3D source mesh object in a direction that is downwards by half of a depth of the 3D source mesh object.

3. The method as in claim 2, further comprising:
generating the 3D source mesh object by a three-dimensional-augmented-reality engine from medical data, the 3D source mesh object being encoded in byte format, the medical data selected from computed tomography scan data, magnetic resonance image scan data, which is a fundamental object that represent characters, props and scenery, which acts as a container for components which define behavior and implement functionality;
generating the copy mesh object by copying the 3D source mesh object; and
calculating a center of the 3D source mesh object from the 3D source mesh object.

4. The method as in claim 2, wherein generating the scene mesh object further comprises:
transforming unstructured environment data from a room scan and converting into an abstract representation.

5. An apparatus for augmented reality, the apparatus comprising:
a microprocessor;
a generator of a 3D source mesh object from two-dimensional (2D) or three-dimensional (3D) medical image data, the generator of the 3D source mesh object being operably coupled to the microprocessor;
a calculator of a center of the 3D source mesh object, the calculator being operably coupled to the generator of the 3D source mesh object;
a generator of an orientation bar that is placed orthogonal to the surface of the 3D source mesh object at a center of the 3D source mesh object, the generator of the orientation bar being operably coupled to the calculator;
a generator of a scene mesh object being operably coupled the generator of the orientation bar;
a generator of a patient mesh object that cuts the scene mesh object in reference to original dimensions of the 3D source mesh object, the generator of the patient mesh object being operably coupled the generator of the scene mesh object; and
a displayer of the patient mesh object, wherein the displayed patient mesh object includes the orientation bar, the displayer being operably coupled to the generator of the patient mesh object.

6. The apparatus as in claim 5, further comprising:
a calculator of a new position of the patient mesh object in terms of x, y and z coordinates, the calculator or the new position being operably coupled to the displayer of the patient mesh object;
a rotator of the patient mesh object, yielding a rotated patient mesh object, wherein the patient mesh object is rotated in reference to two points, the rightmost and the leftmost points from the patient mesh object, the rotator being operably coupled to the calculator of the new position;
a displayer of the rotated patient mesh object, the displayer of the rotated patient mesh object being operably coupled to the rotator.

7. The apparatus as in claim 5, wherein implemented as a component of mixed reality smartglasses.

8. The apparatus as in claim 5, wherein the orientation bar is yellow colored and between 1 cm and 1 meter in length.

9. The apparatus as in claim 5, wherein the orientation bar is between 10 cm and 1 meter in length.

10. The apparatus as in claim 5, wherein the orientation bar is a color other than yellow.

11. The apparatus as in claim 5, wherein the orientation bar is yellow colored and between 10 cm and 1 meter in length.

12. The apparatus as in claim 5, wherein the generator of the patient mesh object that cuts the scene mesh object places the 3D source mesh object in a direction that is downwards by half of a depth of the 3D source mesh object respective to each axis and the orientation of a patient, an initial orientation of a human from an operator, an original size from the 3D source mesh object, and a location marked by the operator's right index fingertip.

* * * * *